United States Patent [19]

Stoner et al.

[11] 4,064,629
[45] Dec. 27, 1977

[54] CAVITY LINER FOR DENTAL RESTORATIONS

[75] Inventors: Glenn E. Stoner; Lyle D. Zardiackas, both of Charlottesville, Va.

[73] Assignee: The University of Virginia, Charlottesville, Va.

[21] Appl. No.: 652,238

[22] Filed: Jan. 26, 1976

[51] Int. Cl.$^2$ ................................................ A61K 5/01
[52] U.S. Cl. ........................................... 32/15; 106/35
[58] Field of Search ...................... 32/15, 10 A; 106/35

[56] References Cited

U.S. PATENT DOCUMENTS

| | | | |
|---|---|---|---|
| 3,254,411 | 6/1966 | Shelley | 32/15 |
| 3,509,089 | 4/1970 | Dougherty | 106/35 |

FOREIGN PATENT DOCUMENTS

| | | | |
|---|---|---|---|
| 2,088,060 | 1/1972 | France | 32/15 |

*Primary Examiner*—Russell R. Kinsey

*Attorney, Agent, or Firm*—Oblon, Fisher, Spivak, McClelland & Maier

[57] ABSTRACT

Dental restorations are prepared by preparing a cavity within a carious tooth for receiving a dental amalgam filling;

coating the surfaces of the cavity with a layer of an adhesive-metal lining composition, the metal of the composition being characterized by the capability of being amalgamated by diffusion of the mercury from a subsequently applied dental amalgam filling, and which is further characterized by a corrosion resistance which is higher than the corrosion resistance of the subsequently applied dental amalgam filling; and packing the remaining adhesive-metal coated cavity with Ag-Hg-Sn dental amalgam, whereby free mercury present in the amalgam is diffused into, and amalgamates with the metal of the adhesive-metal lining coating, so as to form an integral restoration of the dental amalgam and the coating, and the adhesive effectively promotes bonding between the integral restoration and the cavity surfaces.

8 Claims, No Drawings

CAVITY LINER FOR DENTAL RESTORATIONS

BACKGROUND OF THE INVENTION

1. Field Of The Invention

The present invention relates to a method for filling prepared dental cavities in a manner which substantially reduces corrosion at the interface of the tooth-amalgam restorations. More particularly, the present invention relates to a cavity lining material containing an adhesive which not only improves the tenacity of the bonding of a dental restoration to cavity surfaces, but also is effective in substantially reducing the susceptibility of amalgam fillings to corrosion.

2. Description Of The Prior Art

Normally, dental cavities are filled with a silver-tin amalgam. With time, however, the amalgam restoration degenerates by corrosion and, as a result, it must be replaced.

Silver-tin dental amalgam is produced by triturating or mixing about equal quantities of the powdered silver-tin alloy, principally $Ag_3Sn$, and Hg. The mixture, when placed in a cavity, hardens to form several alloy phases. Of the phases which form, the two which predominate are a silver-mercury phase, $Ag_2Hg_3$ ($\gamma_1$) and a tin-mercury phase, $Sn_{7.8}Hg$ ($\gamma_2$). Over a period of time, the tin from the $\gamma_2$ phase dissolves or corrodes because tin is less noble (more easily oxidized) than either Ag or Hg and because of factors such as differential aeration. This corrosion, of course, reduces the strength of the amalgam restoration, causes discolorization of the tooth, and contributes to marginal discrepancies and eventual partial extrusion of the restoration from the cavity.

Differential aeration causes the corrosion process (i.e., tin dissolution) to occur most rapidly in areas of lower oxygen concentration. Thus, the primary area of corrosion is at the restoration-tooth interface. Corrosion of the margins (that part of the restoration-tooth interface that is exposed to saliva) is especially critical as such corrosion contributes to recurrent decay. Thus, the corrosion process usually occurs from the inside-out, which weakens the restoration.

Differential aeration is a common oxidative phenomenon. For instance, it is the mechanism which causes rust to spread circumferentially under the paint around a pin-hole blemish on painted steel. In a dental restoration, the first step of differential aeration is the reduction of oxygen on the unexposed restoration-tooth interface. Mercury and silver are relatively inert in comparison to tin and only participate as sites for oxygen reduction. The anodic oxidation (corrosion) of the surface tin atoms causes an electron transfer to occur from the tin atoms at the surface of the amalgam restoration. These electrons are conducted to the exposed (oxygen rich) surface of the amalgam through the amalgam bulk, resulting in the cathodic reduction of oxygen atoms. The net effect is that the oxidation of tin atoms, which occurs on the unexposed (to air) amalgam surface, results in the generation of tin ions within the interface. In addition, the presence of the tin ions in the areas adjacent to the cavity surfaces promotes further deterioration of the dental restoration by the precipitation of tin hydroxides which cause the area to become more acid.

One of the reasons that the silver-tin ($Ag_3Sn$) alloy is used is that the resulting amalgam is reasonably strong and expands or contracts very little upon hardening. Because tin is less noble than silver or mercury, and because the atomic proportions of tin and mercury in the $\gamma_2$ phase ($Sn_{7.8}Hg$) are unfavorable, it is essentially the only part of the amalgam that corrodes. Hence, the corrosion of dental amalgam restorations seems to be a result of differential aeration, and of the presence of tin in the $\gamma_2$ phase.

The inventors in an earlier patent application have described a method for preparing the surface of dental cavities so that the dental amalgam which is used to fill the cavity exhibits a substantially reduced tendency to deteriorate over long periods of time. The method involves the application of a liner of a metal such as silver which will amalgamate with mercury to the cavity surfaces prior to filling the cavity proper with dental amalgam. Mercury diffuses from the amalgam bulk into the metal liner so that a metal alloy region is formed between the amalgam and cavity surfaces which is free of tin atoms. Differential aeration, therefore, cannot occur in this region and consequently, dental restorations prepared in this manner possess longer effective lifetimes than conventional dental restorations.

A continuing problem with dental restorations is, that despite the improvements described above concerning the improved stability of dental restorations, a need continues to exist for a method of improving the bonding strength of dental restorations to cavity surfaces while at the same time exhibiting substantial corrosion resistance.

One prior art technique of attempting to improve the bonding strength between dental restorations and cavity surfaces as shown by Saffir in U.S. Pat. No. 3,513,123 involves the application of a cavity lining composition consisting of an epoxy resin and a dental alloy or amalgam prior to filling of the cavity with an amalgam. While the lining material may promote adhesion between the applied dental restoration and the cavity surfaces, the overall restoration exhibits the same susceptibility to corrosion as conventional restorations.

Another technique of attempting to improve the adhesion of dental restorations to cavity surfaces as described in *Union Broach* (1972) involves the application of a silver lining to cavity surfaces prior to filling the cavity with dental amalgam from a composition of silver in a eugenol base. While the silver lining improves adhesion of the dental amalgam to the cavity surfaces, the resistance of the filling to deterioration by oxidation is not improved over conventional dental restorations because the relatively high amounts of eugenol in the composition interfere with the effective bonding of the amalgam with the liner.

Yet another prior art method is known for the filling of pits and fissures in teeth as disclosed by Takeuchi, U.S. Pat. No. 3,518,762 in which a monomeric lower alkyl α-cyanoacrylate is first applied to the pit or fissure and thereafter, microfine particles of a material such as gold, silver, tin or the like which may be in admixture with or coated with a lower alkyl methacrylate polymer are applied to the pit or fissure to complete the filling. The composition, however, is used to prevent carious formation in teeth and is not used in the preparation of dental restorations.

A need, therefore, continues to exist for a technique of both improving the adhesion of dental amalgams in prepared cavities as well as improving the resistance of the same to corrosion.

SUMMARY OF THE INVENTION

Accordingly, one object of the present invention is to provide a method for improving the adhesion of dental restorations to cavity surfaces while at the same time improving the resistance of the restorations to deterioration.

Briefly, this object and other objects of the invention, as hereinafter will become more readily apparent, can be attained by a method for applying dental restorations by preparing a cavity within a cavious tooth for receiving a dental amalgam filling; coating the surfaces of the cavity with a layer of an adhesive-metal lining composition, said metal of the composition being characterized by the capability of being amalgamated by diffusion of the mercury from a subsequently applied dental amalgam filling, and which is further characterized by a corrosion resistance which is higher than the corrosion resistance of the subsequently applied dental amalgam filling; and packing the remaining adhesive-metal coated cavity with Ag-Hg-Sn dental amalgam, whereby free mercury present in the amalgam is diffused into, and amalgamates with the metal of the adhesive-metal lining coating, so as to form an integral restoration of the dental amalgam and the coating and the adhesive effectively promotes bonding between the integral restoration and the cavity surfaces.

DETAILED DESCRIPTION OF THE PREFERRED EMBODIMENTS

In the process of forming dental restorations for carious teeth, a cavity is prepared in the carious tooth and the cavity is filled with a dental amalgam which is most usually a mixture of mercury, tin and silver. As the metal mixture hardens in the cavity, a variety of interpenetration compounds or phases form, of which three predominate. The predominant phases are a $\gamma$ phase, a silver mercury phase, $Ag_2Hg_3(\gamma_1)$ and a tin-mercury phase, $Sn_{7-8}Hg$ ($\gamma_2$). As the filling sets, the silver rich $\gamma_1$ phase expands and the tin rich $\gamma_2$ phase contracts which are counterbalancing forces resulting in a very small net change in volume.

Of the metals in the amalgam, silver and mercury are stable elements in that they are very resistant to oxidation and thus none of the $\gamma_1$ phase dissolves or is removed from the filled tooth. The other principal phase, that is the $\gamma_2$ phase, is not as stable as the $\gamma_1$ phase, and will dissolve from the tooth because tin is relatively easily oxidized.

Applicants, as described in an earlier patent application, Ser. No. 478,302, filed June 11, 1974, herein incorporated by reference, have found that if the surfaces of a prepared dental cavity are coated with a metallic film of a metal more positive than tin in the International Electromotive Series such as silver, gold, platinum, indium, copper, or alloys thereof, or alloys with another metal inert to the system, and then the lined cavity is filled with dental amalgam, a restoration is formed which is extremely resistant to corrosion and exhibits superior lifetimes compared to conventional restorations. It is believed that mercury from the bulk of the amalgam diffuses into the metal of the lining whereby an alloy zone forms next to the cavity surfaces which is free of tin atoms. Consequently, the region adjacent the cavity surfaces does not corrode because no tin atoms are present to undergo oxidation.

This prior discovery forms the basis for the method of the present invention wherein it has now been found that certain adhesives, when mixed with the oxidation-resistant metal or alloy of the prior invention, form an adhesive-metal lining composition, which when applied to the surfaces of a tooth cavity, results in an exceptionally tightly bound dental restoration to the cavity surfaces and a restoration which exhibits the long effective lifetimes characteristic of the restorations of the earlier invention. The applied liner achieves two important objectives which are the inhibition of corrosion of the restoration and the improvement of the adhesion of the subsequently applied amalgam to the tooth by chemical or mechanical adhesion means. Suitable adhesive materials satisfactory for oral application include polycarboxylate cements such as polyacrylates containing zinc oxide and polyacrylic acid, zinc polyacrylate cements in which up to 25 wt% of the zinc oxide is substituted with magnesium oxide, bis-GMA which may be synthesized from the reaction of bisphenol A and glycidyl methacrylate; zinc oxide-eugenol; zinc oxide eugenol-o-ethoxybenzoic acid; zinc phosphate; copper phosphate; silicate cements which are mixtures of complex glass alumino-silicates containing magnesium, fluorine, calcium, sodium and phosphorous; zinc silicophosphates, polyacrylates containing mineral fillers, and the like. The amount of adhesive combined with the metal or alloy is less than 55 wt%, preferably 25% to 50%. If the amount of adhesive exceeds the maximum amount indicated, the adhesive will decrease the amount of silver in the liner that is available for amalgamation with the amalgam. Bonding will take place but the improved bonding of the present composition will not be as readily attained. If the amount of adhesive is less than 25%, the amount of adhesive available for bonding at the tooth-liner interface decreases so that the improved bonding effects of the present invention are not as readily attained. Instead, if less than 25% adhesive is used, bonding of the liner to the cavity surface becomes increasingly dependent upon the mechanical bonding forces derived from contact of the irregular cavity walls with the surface of the liner.

The major criteria is the selection of a dental adhesive for the purposes of the present invention are that, besides its compatability with tooth structure and the necessity of the adhesive meeting FDA and ADA specifications, once the adhesive liner has formed in the tooth cavity, the applied lining must permit the diffusion of mercury from the subsequently applied amalgam into the liner whereupon the amalgam constituents interact with the metal of the liner to form an integral restoration.

The metal or alloy which is combined with adhesive in the composition applied to the cavity surfaces are those metals and alloys which will amalgamate by diffusion of the mercury from the subsequently applied dental amalgam, so as to become an integral part of the amalgam, and which is characterized by a corrosion resistance which is greater than the dental amalgam. Preferred metals include those metals which are more positve than tin in the International Electromotive Series. For instance, suitable metals include platinum, gold, copper, indium, silver, alloys thereof, or alloys with another metal inert to the system. Most preferred, however, are silver and alloys containing silver.

The dental composition can be completed by adding trace amounts, that is, up to about 0.1 wt% of a wetting agent such as lecithin and a solvent such as acetone, chloroform, methylchloroform, the lower alkyl alcohols, the lower alkyl ethers or the like, wherein the lower alkyl groups contain from one to six carbon atoms, to the adhesive-metal combination. The particle size of the metal particles should be less than 400 mesh, preferably less than 1μ. The amount of metal or alloy in the liner composition should be greater than 45 wt%, preferably 50 to 75 wt%.

The adhesive-metal liner can be deposited on the surfaces of the cavity in the form of a paste, paint or slurry which is thin enough to apply a homogeneous coat on the cavity. The composition deposited can be a metal containing adhesive and the only materials in the liner composition are metal adhesive and possibly a wetting agent and a solvent. In actual practice the composition is formed by mixing the two parts of the adhesive immediately prior to application of the composition to the prepared cavity. The two parts of the adhesive are mixed in the form of a liquid with powder or in the form of liquid with liquid. The metal to be deposited as well as the wetting agent can be combined with either one or both of the adhesive components. Once the adhesive components are mixed, the adhesive usually hardens rather quickly.

The composition which is applied to the surfaces of the cavity must be thin enough to be applied by such conventional techniques as brushing, swabbing, wiping or the like. Usually, the composition in whatever form is best applied to the cavity by the application of a single coat with a small brush.

The total film thickness of the applied liner composition can vary depending upon the particular adhesive used. Furthermore, complete amalgamation may not be necessary, but complete amalgamation at the amalgam-liner interface is imperative. Generally, the thickness of the liner is less than 100 μm or less than 10% of the smallest dimension of the restoration containing composite.

After the surfaces of the tooth cavity have been coated to the appropriate depth with a layer of the metal or metal alloy particle, a standard dental amalgam is then inserted into the remaining lined cavity by standard dental procedures. Usually, the dental amalgams contain Ag, Hg, and Sn, and often small portions of Cu and Zn. The basic composition of the amalgams used are conventional. The Hg is usually present in an amalgam in an amount of from 45 to 60% before insertion. When the amalgam is packed into the cavity, free mercury will be expressed to the surfaces and to the amalgam-lining interface. The free mercury is highly reactive and will quickly diffuse into the lining metal to form a metal-mercury phase, and to mutually fuse the particles together to form a continuous coating. This process continues thereafter for some period due to the difference in Hg concentration between the applied amalgam and the lining. The result of this amalgamation of the metal in the lining is to form an integral structure of applied amalgam and the lining amalgam, wherein the outermost layer of the integral structure is essentially free of tin, and consequently free of $\gamma_2$tin-mercury phase. The restoration is therefore characterized by a continuous structural integrity and outstanding corrosion resistance.

In conventional restorations which do not use a liner, the free mercury which is expressed at the surface of the restoration increases the problem of deterioration of the restoration. However, when the liner of the present invention is applied to a tooth cavity, the free mercury expressed when the amalgam is applied combines with the metal of the liner resulting in an overall decrease in the concentration of free mercury at the tooth-restoration interface. Consequently, a more stable restoration is achieved.

The cavity liner further has the characteristic that the adhesive component of the applied composition results in a much stronger adhesion of the internal amalgam surfaces to the surfaces of the cavity. Bonding of the restoration to the cavity walls is also enhanced by the fact that as the mercury diffuses into the metal lining, the metal tends to expand, and tends to fill any crevices or irregularities in the tooth walls. This is an especially unqiue attribute in the technology of linings for dental fillings. The successful amalgamation of the metal of the lining composition with the bulk of the applied dental amalgam is perhaps somewhat surprising since it might have been expected that the presence of the adhesive in the lining composition might interfere with the necessary amalgamation of the metal in the lining by the diffusion of mercury from the bulk of the applied amalgam. Yet, successful amalgamation occurs. It may be that the adhesives used are of sufficient porosity to achieve amalgamation, or perhaps the amalgamation is achieved due to the small metal particle size.

In addition, since the standard dental amalgams have particle sizes on the order of 40 μm, relatively large spaces exist at the tooth restoration interface. Thus, by using liner compositions containing small metal particles, not only is the reaction time increased between amalgam and liner, but also much closer juxtaposition of the liner to the tooth wall is achieved.

Having generally described the invention, a further understanding can be obtained by reference to certain specific examples which are provided herein for purposes of illustration only, and are not intended to be limiting unless otherwise specified.

EXAMPLE 1

The purpose of this experiment was to determine if a dental amalgam could be bonded to tooth structure. A metal containing adhesive was prepared using <1 μm Ag particles and two commercially available polycarboxylate dental cements, Durelon and PCA. The cement was prepared using a 1:1 ratio of cement powder/liquid, to which was added the Ag powder to give a total wt% Ag of 50 w/o. To the mixture was added ethyl alcohol in amounts sufficient to make the liner composition thin enough to paint onto the surface of an extracted tooth. After the mixture was allowed to set, a 5mm × 3mm × 3mm wax mold was placed on the painted tooth surface. The mold exposed an area to be filled approximately one half of which was dentin and the other half of which was enamel. A conventional dental amalgam having an original content of 53 w/o Hg was then hand condensed into the wax mold in a stepwise procedure using a 2 kg balance apparatus. After 2 hours the wax mold was removed and the dental amalgam was bonded to the tooth structure.

EXAMPLE 2

The following experiment was conducted to determine if a bond between the silver containing dental adhesive and a conventional dental amalgam could be attained. Metal containing adhesive was formed using <1 μm spherical Ag particles and two commercially available dental polycarboxylate cements, Durelon and PCA. The cement was prepared according to manufacturers specifications using a 1 : 1 wt ratio of powder to liquid. To this was added ≦1 μm Ag particles to give a total wt.% Ag of 50 w/o. To this mixture was added ethyl alcohol in amounts sufficient to make the composition thin enough to paint onto the surface of a glass slide. The painted glass slide was allowed to dry and used as the base of a 12mm × 5mm × 1mm mold. A conventional dental analgam was then hand condensed into the mold as per Example 1. The reaction between the mercury expressed during hand condensing and the silver in the liner was observed occuring through the glass slide and appeared to be complete after approximately 2 hours. At this time the mold was removed and it was found that the analgam was bonded to the metalic adhesive liner.

EXAMPLE 3

The procedure of Example 2 was followed with the exception that the w/o silver was varied to 54 w/o, and 61 w/o. The same bonding results were obtained between liner and amalgam as were obtained in Example 2.

EXAMPLE 4

The same procedure described in Example 2 was followed with the exception that the polycarboxylate adhesive was replaced by a commercially available dental zinc phosphate cement "Tenicin." This cement was prepared using a powder to liquid ratio of approximately 2.5 : 1 and then adding distilled water in an amount equal to the liquid in the adhesive. To the prepared adhesive was added the <1 μm Ag particles to give a final mixture of 50 w/o Ag. The results obtained are the same as those obtained in Example 2.

EXAMPLE 5

The following tests were run to measure the shear strength of the amalgam composite liner interface. A composite liner was prepared as per Example 1 except that in addition to a 50 w/o Ag containing adhesive, 45 w/o, 54 w/o and 61 w/o adhesives were prepared. Each prepared metallic liner was painted onto the circumferential surface of a 4 mm diameter hole drilled through 3 mm plexiglass using a carbide drill. Into all 80 of the holes plus 20 identically prepared non-lined holes was hand condensed a conventional dental amalgam as described in Example 1. Samples and molds were placed in 1.0 w/o NaCl for 7 days. The samples were then ejected from the molds using an Instron Tensile Testing machine. The results obtained are as follows:

a. A significant increase in the retention of lined samples over unlined samples was found with an increase in shear strength of 5 to 7 times.

b. Fracturing occurred through the liner or at the liner-mold interface above 45 w/o Ag.

EXAMPLE 6

The procedure of Example 6 was repeated except that the liner was prepared as described in Example 4. The results showed a significant increase in shear strength of 2-3 times with fracture occuring through the liner or at the liner-mold interface.

EXAMPLE 7

X-ray energy analysis and Scanning Electron Miscroscopy of the samples described in Example 5 showed the following results:

1. The surface of the lined sample contained none of the corrosive $\gamma_2$ phase present in dental analgam and only contained Ag and Hg.

2. The analysis showed that the liner thickness varied between 20 and 100 μm in all samples examined.

Having now fully described the invention, it will be apparent to one of ordinary skill in the art that many changes and modifications can be made thereto without departing from the spirit or scope of the invention as set forth herein.

What is claimed as new and intended to be secured by Letters Patent is:

1. A method for applying dental restorations, which comprises:

preparing a cavity within a carious tooth for receiving a dental mercury-containing amalgam filling;

coating the surfaces of said cavity with a layer of an adhesive-metal lining composition consisting essentially of the combination of greater than 46 wt.% of at least one finely divided pure metal at a position higher than tin on the International E.M.F. Series characterized by a corrosion resistance which is higher than the corrosion resistance of said subsequently applied dental amalgam and which has a capability of being amalgamated by diffusion of the mercury into said lining and which has a particle size of less than 400 mesh, with less than 54 wt.% of an ahesive selected from the group consisting of polycarboxylate cements, zinc silico-phosphate, zinc phosphate, copper phosphate, silicate, zinc oxide-eugenol, zinc oxide-eugenol-o-ethoxybenzoic acid, and a resin, to a thickness of less than 100 μ, wherein said composition contains up to about 0.1 wt.% of a wetting agent and a volatile solvent in the final dried form; and packing said remaining adhesive-metal coated cavity with a Ag-Hg-Sn dental amalgam, whereby free mercury present in said amalgam is diffused into and amalgamates with said metal of said adhesive-metal lining coating so as to form an integral restoration of said dental amalgam and said coating which is corrosion resistant and said adhesive effectively promotes adhesion between said integral restoration and said cavity surfaces.

2. The method of claim 1, wherein said metal is selected from the group consisting of Pt, Ag, Cu, In, Au, or alloys thereof, and alloys thereof with another metal which is inert to the system.

3. The method of claim 2, wherein said metal is Ag.

4. The method of claim 2, wherein said metal is Au.

5. The method of claim 2, wherein said metal is Cu.

6. The method of claim 1, wherein the thickness of said coating is less than 10% of the smallest dimension of the restoration.

7. A metal containing composition suitable as a corrosion resistant metal liner for the surfaces of a prepared cavity of a carious tooth, which consists essentially of:

a combination of greater than 46 wt.% of at least one finely divided pure metal at a position higher than tin on the International E.M.F. Series, characterized by a corrosion resistance which is higher than the corrosion resistance of a subsequently applied Ag-Hg-Sn containing dental amalgam and which has the capability of being amalgamated by diffusion of the mercury into said lining and which has a particle size of less than 400 mesh, with less than 54 wt.% of an adhesive selected from the group consisting of polycarboxylate cements, zinc silico-phosphate, zinc phosphate, copper phosphate, silicate, zinc oxide-eugenol, zinc oxide-eugenol-o-ethoxybenzoic acid, and a resin, which effectively promotes bonding between said integral restoration and said cavity surface wherein said composition contains up to about 0.1 wt.% of a wetting agent and a volatile solvent in final dried form.

8. The composition of claim 7, wherein said metal is selected from the group consisting of Pt, Ag, Cu, In, Au, or alloys thereof, and alloys thereof with another metal which is inert to the system.

* * * * *

UNITED STATES PATENT AND TRADEMARK OFFICE
CERTIFICATE OF CORRECTION

PATENT NO. : 4,064,629
DATED : December 27, 1977
INVENTOR(S) : Glenn E. Stoner et al It is certified that error appears in the above-identified patent and that said Letters Patent are hereby corrected as shown below:

Column 1, line 4, after "BACKGROUND OF THE INVENTION", please insert the following new paragraph:

--The invention described herein has been made in the course of or as a result of a contract from the Department of Health, Education and Welfare.--

Signed and Sealed this

Twenty-ninth Day of August 1978

[SEAL]

Attest:

RUTH C. MASON
Attesting Officer

DONALD W. BANNER
Commissioner of Patents and Trademarks